(12) United States Patent
Dikstein

(10) Patent No.: US 8,912,166 B2
(45) Date of Patent: Dec. 16, 2014

(54) EYE DROPS FOR TREATMENT OF CONJUNCTIVOCHALASIS

(71) Applicant: Resdevco Research and Development Co. Ltd., Jerusalem (IL)

(72) Inventor: Shabtay Dikstein, Jerusalem (IL)

(73) Assignee: Resdevco Research and Development Co. Ltd., Jerusalem (IL)

( * ) Notice: Subject to any disclaimer, the term of this patent is extended or adjusted under 35 U.S.C. 154(b) by 0 days.

(21) Appl. No.: 14/071,934

(22) Filed: Nov. 5, 2013

(65) Prior Publication Data

US 2014/0057983 A1 Feb. 27, 2014

Related U.S. Application Data

(63) Continuation-in-part of application No. PCT/IL2012/000157, filed on Apr. 5, 2012.

(30) Foreign Application Priority Data

May 5, 2011 (IL) .......................................... 212725

(51) Int. Cl.
*A61K 31/715* (2006.01)
*A61K 31/70* (2006.01)
*A61K 9/48* (2006.01)
*A61K 31/047* (2006.01)
*A61K 9/00* (2006.01)
*A61K 31/196* (2006.01)

(52) U.S. Cl.
CPC ............. *A61K 31/047* (2013.01); *A61K 9/0048* (2013.01); *A61K 31/196* (2013.01)
USPC ............................ 514/54; 514/62; 424/78.04

(58) Field of Classification Search
CPC .... A61K 31/715; A61K 31/70; A61K 9/0048
USPC ..................... 514/54, 62; 424/78.04
See application file for complete search history.

(56) References Cited

U.S. PATENT DOCUMENTS

| 5,106,615 | A | 4/1992 | Dikstein |
| 5,795,913 | A | 8/1998 | Lehmussaari et al. |
| 2007/0212420 | A1 | 9/2007 | Xia et al. |
| 2010/0086512 | A1 | 4/2010 | Schaefer |

FOREIGN PATENT DOCUMENTS

| CN | 1488404 | A | 4/2004 |
| CN | 101940701 | A | 1/2011 |
| EP | 2078527 | A1 | 7/2009 |
| WO | 0001365 | A1 | 1/2000 |
| WO | 2005067892 | A1 | 7/2005 |
| WO | 2006119174 | A1 | 11/2006 |
| WO | 2006123324 | A1 | 11/2006 |

OTHER PUBLICATIONS

Gao et al., "Composition comprising sodium hyaluronate and glycerin, useful as eye drops", Database WPI Section Ch, Week 200442, Apr. 14, 2004, Thomson Scientific, London, GB.

Zhou, "Ointment useful for preventing and/or treating e.g. pterygium, comprises Aloe gel, aloin, alamycin, carbomer, sodium hyaluronate, anthraquinone compound and free amino acids", Database WPI Section CH, Week 201124, Thomson Scientific, London, GB.

Meller et al., "Conjunctivochalasis: Literature review and possible pathophysiology", Survey of Ophthalmology, Nov. 1998, pp. 225-232, vol. 43, No. 3.

Solomon et al., "The effect of a new tear substitute containing glycerol and hyaluronate on keratoconjunctivitis sicca", Journal of Ocular Pharmacology and Therapeutics, Dec. 1998, pp. 497-504, vol. 14, No. 6.

Braunschweig, Ueber Faltenbildung der Conjunctiva bulbi, Klin. Monatsbl. Augenheilkd. 1921, pp. 123-124, 66.

Hughes, W. L. Conjunctivochalasis, Am. J. Opthamol. 1942, pp. 48-51, 25.

Yokoi et al., Clinical Impact of Conjunctivochalasis on the Ocular Surface, Cornea, Nov. 2005, pp. S24-S31, vol. 24 (supp 1).

International Search Report dated Aug. 31, 2012 in corresponding International Application No. PCT/IL2012/000157.

*Primary Examiner* — Raymond Henley, III

(74) *Attorney, Agent, or Firm* — The Law Office of Michael E. Kondoudis

(57) ABSTRACT

An ophthalmic preparation and method, usable to treat conjunctivochalasis. The ophthalmic preparation comprises an aqueous solution of glycerol. The preparation may also include additional components including high molecular weight polymers for viscosity control and pharmacologically active substances. The method includes administering an ophthalmic preparation including an aqueous solution of glycerol to a patient.

16 Claims, No Drawings

EYE DROPS FOR TREATMENT OF CONJUNCTIVOCHALASIS

REFERENCE TO RELATED APPLICATIONS

This application is a Continuation-in-Part of International Application No. PCT/IL2012/000157, filed Apr. 5, 2012, and claims priority from Israeli Patent Application No. 212725, filed May 5, 2011.

FIELD OF THE INVENTION

This invention relates to non-surgical methods for treatment of conjunctivochalasis. In particular, it relates to eye drops comprising a solution of glycerol useful for treatment of conjunctivochalasis.

BACKGROUND OF THE INVENTION

Conjunctivochalasis, a condition characterized by excess folds of the conjunctiva, is of relatively common occurrence, especially in the elderly and in contact lens wearers. It can be a serious condition and in extreme cases requires surgical intervention. See, for example, (a) Braunschweig, *Klin. Monatsbl. Augenheilkd.* 1921, 66, 123-124; (b) Hughes, W. L. *Am. J. Opthamol.* 1942, 25, 48-51; and (c) P. Yokoi, N.; Komuro, A.; Nishii, M.; Inagaki, K.; Tanioka, H.; Kawasaki, S.; Kinoshita, S. *Cornea,* 2005, 24 (supp. 1), S24-S31, each of which is incorporated in its entirety by reference.

While various diseases of the eye can be treated by the application of liquid preparations administered to contact the eye, no recognized treatment of conjunctivochalasis by eye drops alone is known.

SUMMARY OF THE INVENTION

The present invention provides eye drops useful in the treatment of or alleviation of symptoms of conjunctivochalasis which may spare surgical intervention. The eye drops are based on the use of glycerol, preferably in isotonic or nearly isotonic solution. These isotonic solutions can further comprise additional ophthalmologic medications. Glycerol is itself a humectant, i.e. is capable of holding water.

According to a preferred embodiment of the invention, the eye drops comprise isotonic concentrations of glycerol. In additional preferred embodiments of the invention, a polymer of molecular weight greater than 10,000 Dalton is added in order to increase the viscosity. If the polymer is anionic, then in the absence of added inorganic salt, the solution has the additional advantage of having a non-Newtonian viscosity profile. In some embodiments of the invention, the eye drops consist of an isotonic solution of glycerol and optionally one or more ingredients selected from the group consisting of (a) polymers of molecular weight greater than 10,000 Dalton; (b) pharmaceutically effective amount of at least one additional ophthalmologic medication; (c) stabilizers; (d) preservatives; (e) antioxidants; and (f) buffers.

In some embodiments of the invention, the eye drops additionally comprise a pharmaceutically effective amount of at least one additional ophthalmologic medication. In an exemplary embodiment, the eye drops additionally comprise diclofenac.

It is therefore an object of this invention to disclose an ophthalmic preparation comprising an aqueous solution of glycerol, wherein said ophthalmic preparation is an effective non-surgical treatment for conjunctivochalasis.

It is a further object of this invention to disclose such an ophthalmic preparation, wherein said solution is essentially isotonic.

It is a further object of this invention to disclose such an ophthalmic preparation as defined in any of the above, wherein said solution has a pH of about 7.

It is a further object of this invention to disclose such an ophthalmic preparation as defined in any of the above, wherein the salt concentration is less than about 2 mM.

It is a further object of this invention to disclose such an ophthalmic preparation as defined in any of the above, further comprising a polymer of molecular weight of at least 10,000 Dalton.

It is a further object of this invention to disclose such an ophthalmic preparation, wherein the concentration of said polymer is chosen to bring said solution to a predetermined viscosity.

It is a further object of this invention to disclose such an ophthalmic preparation, wherein said polymer is anionic.

It is a further object of this invention to disclose such an ophthalmic preparation, wherein said polymer is chosen from the group consisting of hyaluronate or carbomer.

It is a further object of this invention to disclose such an ophthalmic preparation as defined in any of the above, further comprising a pharmaceutically effective amount of a pharmacologically active agent.

It is a further object of this invention to disclose such an ophthalmic preparation, wherein said pharmacologically active agent is diclofenac.

It is a further object of this invention to disclose such an ophthalmic preparation, further comprising at least one substance selected from the group consisting of stabilizers, preservatives, antioxidants, and buffers.

It is a further object of this invention to disclose such an ophthalmic preparation as defined in any of the above, wherein said ophthalmic preparation does not comprise any oil in water or wax in water emulsion.

It is a further object of this invention to disclose such an ophthalmic preparation as defined in any of the above, wherein application of said preparation between one and five times daily reduces the severity of the symptoms of conjunctivochalasis as measured by the LIPCOF scale.

It is a further object of this invention to disclose such an ophthalmic preparation as defined in any of the above, wherein application of said preparation three times daily reduces the severity of the symptoms of conjunctivochalasis as measured by the LIPCOF scale.

It is a further object of this invention to disclose such an ophthalmic preparation, wherein a statistically significant reduction in the severity of the symptoms of conjunctivochalasis occurs within 6 months of the initiation of said application of said preparation three times daily.

It is a further object of this invention to disclose such an ophthalmic preparation, wherein a statistically significant reduction in the severity of the symptoms of conjunctivochalasis occurs within 1 month of the initiation of said application of said preparation three times daily.

It is a further object of this invention to disclose a non-surgical method of treating or alleviating severity of symptoms of conjunctivochalasis, comprising administering to a patient in need an ophthalmic preparation comprising an aqueous solution of glycerol. In preferred embodiments of the invention, the method comprises administering a patient in need an ophthalmic preparation as defined in any of the above. In the most preferred embodiments of the invention, the method consists of administering a patient in need an ophthalmic preparation as defined in any of the above.

In some preferred embodiments of the method, said step of administering comprises administering said ophthalmic preparation in the form of eye drops.

In some embodiments of the method, said step of administering comprises administering said ophthalmic preparation three times daily until the severity of the symptoms is reduced to an acceptable level. In other embodiments of the method, said step of administering comprises administering said ophthalmic preparation once daily until the severity of the symptoms is reduced to an acceptable level.

DETAILED DESCRIPTION OF THE PREFERRED EMBODIMENTS

In the following description, various aspects of the invention will be described. For the purposes of explanation, specific details are set forth in order to provide a thorough understanding of the invention. It will be apparent to one skilled in the art that there are other embodiments of the invention that differ in details without affecting the essential nature thereof. Therefore the invention is not limited by that which is described in the specification, but only as indicated in the accompanying claims, with the proper scope determined only by the broadest interpretation of said claims.

The invention comprises a solution of glycerol in water. In preferred embodiments of the invention, 2.5 g of glycerol are present in each 100 ml of the prepared solution. In some embodiments of the invention, in the solution the inorganic salt concentration is less than 2 mM. In preferred embodiments of the invention, the glycerol solution is isotonic. In preferred embodiments of the invention, the viscosity of the solution is controlled by addition of a quantity of high molecular weight polymer (MW>$10^4$ Dalton) such as hyaluronate or carbomer sufficient to bring the solution to the desired viscosity. All ingredients are of purity sufficient for use in eye drops.

The solutions are then transferred to a container appropriate for dispensing it as eye drops.

In other embodiments of the invention, the solution additionally comprises a pharmaceutically effective concentration at least one pharmacologically active agent. If necessary, any stabilizer, preservative, antioxidant, buffer or combination thereof appropriate for use with the pharmacologically active agent may be added to the solution in any concentration suitable for use in eye drops.

A typical protocol for use of the resulting eye drops to treat or to alleviate the symptoms of conjunctivochalasis is to place drops in the affected eye 3 times daily until the severity of the symptoms is reduced to an acceptable level. In particularly severe cases, more frequent applications may be necessary, and in less severe cases, a single daily dose may be sufficient.

EXAMPLE 1

A solution was prepared containing:

| | |
|---|---|
| Glycerol | 2.5 g |
| Sodium hyaluronate | 0.1 g |
| Water | sufficient to bring to 100 ml |

The solution was buffered to pH of 7.2.

EXAMPLE 2

A solution was prepared containing:

| | |
|---|---|
| Glycerol | 2.5 g |
| Sodium hyaluronate | 0.015 g |
| Carbomer 481 | 0.015 g |
| Water | sufficient to bring to 100 ml |

The solution was adjusted to about pH of 7.

EXAMPLE 3

A solution was prepared containing:

| | |
|---|---|
| Glycerol | 2.5 g |
| Diclofenac sodium | 0.1 g |
| Water | sufficient to bring to 100 ml |

The solution was buffered to pH of about 7.

EXAMPLE 4

A solution, containing less than 2 mM inorganic salt, was prepared as described in Example 2 above. The solution was then administered on average 3 times daily to a group of patients. The severity of the conjunctivochalasis was measured according to the LIPCOF (Lid Parallel Conjunctival Folds) scale, in which 0 represents the least severe level and 3 is very severe. Determinations of the severity of the conjunctivochalasis were made prior to treatment, one month after the start of treatment, and 6 months after the start of treatment. The results are summarized in Table 1. The changes from the first LIPCOF determination to the second, and from the first to the third, are statistically significant at the $p<0.01$ level.

TABLE 1

| LIPCOF | Prior to treatment | | 1 month | | 6 months | |
|---|---|---|---|---|---|---|
| Grade | N | % | N | % | N | % |
| 0 | 13 | 24.1 | 14 | 26.9 | 12 | 31.6 |
| 1 | 25 | 46.3 | 27 | 51.9 | 22 | 57.9 |
| 2 | 15 | 27.8 | 11 | 21.2 | 4 | 10.5 |
| 3 | 1 | 1.9 | 0 | 0.0 | 0 | 0.0 |

EXAMPLE 5

Twenty patients suffering from conjunctivochalasis who had been using as a palliative measure commercially available artificial tear solutions known in the art were treated with the eye drops of the present invention. Prior to treatment with the eye drops of the present invention, the patients had been using commercially available artificial tear solutions for periods of time ranging from two weeks to three years. Nonetheless, the patients' average LIPCOF score was 2.8, demonstrating that the artificial tear solutions known in the art are ineffective against conjunctivochalasis. The patients were then treated with the eye drops of the present invention, on average 4 times daily. The results of the study are given in Table 2, where the letters A-J represent the different commercially available artificial tear compositions that were used prior to the beginning of treatment with the eye drops of the present invention. After one month of treatment with the eye drops of the present invention, a statistically significant reduction ($p \leq 0.001$) in the average LIPCOF score was obtained, demonstrating the effectiveness of the present invention as a non-surgical treatment for conjunctivochalasis over artificial tear solutions known in the prior art.

TABLE 2

| patient | prior artificial tear treatment | daily regimen | length of prior treatment | LIPCOF grade day 0 right eye | LIPCOF grade day 0 left eye | LIPCOF grade 1 month right eye | LIPCOF grade 1 month left eye |
|---|---|---|---|---|---|---|---|
| 1 | A | | 3 years | 3 | 3 | 3 | 2 |
| 2 | B | 2x | 1 year | 3 | 3 | 2 | 2 |
| 3 | A | 3x | 2 weeks | 2 | 2 | 2 | 2 |
| 4 | C | 5x | 2 years | 3 | 2 | 2 | 1 |
| 5 | C | 4x | 2 years | 3 | 3 | 1 | 2 |
| 6 | D | 3x | 4 months | 3 | 3 | 2 | 2 |
| 7 | — | 2-3x | | 3 | 3 | 3 | 2 |
| 8 | B | | 5 months | 3 | 3 | 2 | 2 |
| 9 | E | 2x | 2 months | 3 | 3 | 1 | 2 |
| 10 | — | 2x | | 3 | 3 | 2 | 2 |
| 11 | C | | 3 years | 2 | 3 | 0 | 1 |
| 12 | A | 3x | 1 year | 3 | 2 | 2 | 1 |
| 13 | A | 3x | 5 months | 3 | 3 | 1 | 1 |
| 14 | B | as needed | 6 months | 3 | 3 | 3 | 2 |
| 15 | A | 2-3x | 2 years | 3 | 3 | 2 | 1 |
| 16 | D | as needed | 4 months | 3 | 2 | 1 | 1 |
| 17 | G | 2x | 2 months | 3 | 3 | 1 | 0 |
| 18 | H | 4x | 1 month | 2 | 3 | 1 | 2 |
| 19 | F | 3x | 1 month | 3 | 3 | 1 | 2 |
| 20 | J | 3x | 1 month | 2 | 3 | 1 | 2 |
| | average LIPCOF grade | | | 2.8 | 2.8 | 1.65 | 1.6 |
| | Variance | | | 0.41 | 0.41 | 0.81 | 0.60 |
| | s.e.m. | | | 0.09 | 0.09 | 0.18 | 0.13 |

I claim:

1. A non-surgical method of treating or alleviating conjunctivochalasis, comprising administering to a patient suffering from conjunctivochalasis, said conjunctivochalasis having a severity characterized by a Lid Parallel Conjunctival Folds (LIPCOF) grade, an ophthalmic preparation comprising an aqueous solution of glycerol until said LIPCOF grade is reduced.

2. The method according to claim 1, wherein said step of administering comprises administering said ophthalmic preparation in the form of eye drops.

3. The method according to claim 1, wherein said step of administering comprises administering said ophthalmic preparation three times daily.

4. The method according to claim 1, wherein said step of administering comprises administering said ophthalmic preparation once daily.

5. The method according to claim 1, wherein said step of administering comprises administering an ophthalmic preparation comprising an aqueous solution of glycerol, wherein said aqueous solution of glycerol is characterized by at least one characteristic selected from the group consisting of:
said solution is essentially isotonic;
said solution has a pH of about 7; and,
said solution has an inorganic salt concentration of less than 2 mM.

6. The method according to claim 1, wherein said ophthalmic preparation comprises an aqueous solution of glycerol and a polymer of molecular weight of at least 10,000 Dalton.

7. The method according to claim 6, wherein said polymer is chosen from the group consisting of hyaluronate and carbomer.

8. The method according to claim 1, wherein said ophthalmic preparation additionally comprises a pharmaceutically effective amount of a pharmacologically active agent.

9. The method according to claim 8, wherein said pharmacologically active agent is diclofenac.

10. The method according to claim 1, wherein said ophthalmic preparation additionally comprises at least one substance selected from the group consisting of stabilizers, preservatives, antioxidants, and buffers.

11. The method according to claim 1, wherein said step of administering comprises administering an ophthalmic preparation comprising an aqueous solution of glycerol that does not comprise any oil in water or wax in water emulsion.

12. The method according to claim 1, wherein said step of administering comprises administering an ophthalmic preparation comprising an aqueous solution of glycerol until said LIPCOF grade is reduced by a statistically significant amount.

13. The method according to claim 1, wherein said step of administering comprises administering an ophthalmic preparation comprising an aqueous solution of glycerol until said LIPCOF grade is reduced by at least one point.

14. The method according to claim 1, wherein said step of administering comprises administering an ophthalmic preparation comprising an aqueous solution of glycerol at least once daily for one month.

15. The method according to claim 14, wherein said step of administering comprises administering an ophthalmic preparation comprising an aqueous solution of glycerol once daily for one month.

16. The method according to claim 14, wherein said step of administering comprises administering an ophthalmic preparation comprising an aqueous solution of glycerol three times daily for one month.

* * * * *